(12) United States Patent
Swanson (10) Patent No.: US 7,455,669 B2
(45) Date of Patent: Nov. 25, 2008

(54) FINGER MOUNTABLE LESION FORMATION DEVICES AND METHODS

(75) Inventor: David K. Swanson, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 401 days.

(21) Appl. No.: 11/075,251

(22) Filed: Mar. 8, 2005

(65) Prior Publication Data

US 2006/0206109 A1    Sep. 14, 2006

(51) Int. Cl.
*A61B 18/14* (2006.01)
(52) U.S. Cl. .......................................... 606/32; 606/41
(58) Field of Classification Search .................. 606/41
See application file for complete search history.

(56) References Cited

U.S. PATENT DOCUMENTS

| 206,474 | A |   | 7/1878  | Morel           |        |
|---------|---|---|---------|-----------------|--------|
| 1,915,721 | A |   | 6/1933  | Diaz            |        |
| 3,845,771 | A |   | 11/1974 | Vise            |        |
| 4,510,939 | A | * | 4/1985  | Brenman et al.  | 600/384|
| 4,685,466 | A |   | 8/1987  | Rau             |        |
| 4,690,148 | A |   | 9/1987  | Hess            |        |
| 4,736,749 | A |   | 4/1988  | Lundback        |        |
| 4,834,090 | A |   | 5/1989  | Moore           |        |
| 5,250,072 | A |   | 10/1993 | Jain            |        |
| 5,443,463 | A |   | 8/1995  | Stern           |        |
| 6,185,442 | B1 |   | 2/2001  | Samson          |        |
| 6,277,117 | B1 |   | 8/2001  | Tetzlaff        |        |
| 6,487,439 | B1 |   | 11/2002 | Skladnev et al. |        |
| 6,652,518 | B2 |   | 11/2003 | Wellman et al.  |        |
| 6,849,075 | B2 |   | 2/2005  | Bertolero et al.|        |
| 6,911,027 | B1 |   | 6/2005  | Edwards         |        |
| 6,926,712 | B2 |   | 8/2005  | Phan            |        |
| 6,932,816 | B2 |   | 8/2005  | Phan            |        |
| 7,020,531 | B1 |   | 3/2006  | Colliou et al.  |        |
| 7,128,741 | B1 | * | 10/2006 | Isaacson et al. | 606/41 |
| 2003/0158547 | A1 |   | 8/2003 | Phan           |        |
| 2004/0260281 | A1 |   | 12/2004 | Baxter, III    |        |
| 2005/0119648 | A1 |   | 6/2005  | Swanson        |        |
| 2005/0215993 | A1 |   | 9/2005  | Phan           |        |
| 2006/0195080 | A1 |   | 8/2006  | Ebert          |        |
| 2007/0093807 | A1 |   | 4/2007  | Baxter         |        |

OTHER PUBLICATIONS

Prosecution History for U.S. Appl. No. 10/079,944 (USPN 6,932,816) including: Notice of Allowance dated Jan. 18, 2005 for U.S. Appl. No. 10/079,944 (USPN 6,932,816), filed Feb. 19, 2002 (6 pages), Amendment dated Dec. 9, 2004 for U.S. Appl. No. 10/079,944 (USPN 6,932,816), filed Feb. 19, 2002 (5 pages).

(Continued)

*Primary Examiner*—Lee S Cohen
(74) *Attorney, Agent, or Firm*—Vista IP Law Group LLP (57) ABSTRACT

An apparatus including a lesion formation element and a carrier configured to mount the lesion formation element on a finger.

19 Claims, 5 Drawing Sheets

OTHER PUBLICATIONS

Non-Final Office Action dated Oct. 4, 2004 for U.S. Appl. No. 10/079,944 (USPN 6,932,816), filed Feb. 19, 2002 (10 pages).
Amendment dated May 14, 2004 for U.S. Appl. No. 10/079,944 (USPN 6,932,816), filed Feb. 19, 2002 (12 pages).
Non-Final Office Action dated Mar. 4, 2004 for U.S. Appl. No. 10/079,944 (USPN 6,932,816), filed Feb. 19, 2002 (6 pages).
Advisory Action dated Feb. 3, 2004 for U.S. Appl. No. 10/079,944 (USPN 6,932,816), filed Feb. 19, 2002 (3 pages).
Amendment dated Jan. 12, 2004 for U.S. Appl. No. 10/079,944 (USPN 6,932,816), filed Feb. 19, 2002 (13 pages).
Final Office Action dated Oct. 8, 2003 for U.S. Appl. No. 10/079,944 (USPN 6,932,816), filed Feb. 19, 2002 (6 pages).
Amendment dated Jul. 14, 2003 for U.S. Appl. No. 10/079,944 (USPN 6,932,816), filed Feb. 19, 2002 (18 pages).
Non-Final Office Action dated Mar. 5, 2003 for U.S. Appl. No. 10/079,944 (USPN 6,932,816), filed Feb. 19, 2002 (8 pages).
Non-Final Office Action dated Sep. 25, 2007 for U.S. Appl. No. 11/067,535, filed Feb. 25, 2005 (7 pages).
Amendment dated Jan. 25, 2008 for U.S. Appl. No. 11/067,535, filed Feb. 25, 2005 (10 pages).
PCT International Search Report dated Apr. 14, 2005 for PCT Application No. PCT/US2004/039283, Applicant Boston Scientific Scimed, form PCT/ISA 210, (3 pages).
PCT Written Opinion for PCT Application No. PCT/US2004/039283, dated Apr. 12, 2005, Applicant Boston Scientific Scimed, form PCT/ISA 210, (7 pages).
PCT International Preliminary Report on Patentability for PCT Application No. PCT/US2004/039283, dated Apr. 12, 2005, Applicant Boston Scientific Scimed, (8 pages).
International Search Report for (PCT/US02/38092), forms PCT/ISA 210 and 220, dated Mar. 28, 2003, Applicant Boston Scientific Scimed, (7 pages).
Written Opinion for (PCT/US02/38092), Form PCT/IPEA 408,dated Mar. 28, 2003 Applicant Boston Scientific Scimed, (5 pages).
International Preliminary Examination Report for PCT/US02/38092, Form PCT/IPEA 416, dated Mar. 12, 2004, Applicant Boston Scientific Scimed, (7 pages).
Prosecution History for 10/727,096 including: Final Office Action dated Nov. 9, 2007 for U.S. Appl. No. 10/727,096 filed Dec. 2, 2003, Applicant Boston Scientific Scimed, (14 pages), Amendment dated Aug. 20, 2007 for U.S. Appl. No. 10/727,096 filed Dec. 2, 2003, Applicant Boston Scientific Scimed, (14 pages).
Non final Office Action dated May 18, 2007 for U.S. Appl. No. 10/727,096 filed Dec. 2, 2003, Applicant Boston Scientific Scimed, (8 pages).
Amendment dated Apr. 27, 2007 for U.S. Appl. No. 10/727,096 filed Dec. 2, 2003, Applicant Boston Scientific Scimed, (11 pages).
Final Office Action dated Feb. 7, 2007 for U.S. Appl. No. 10/727,096 filed Dec. 2, 2003, Applicant Boston Scientific Scimed, (8 pages).
Amendment dated Nov. 9, 2006 for U.S. Appl. No. 10/727,096 filed Dec. 2, 2003, Applicant Boston Scientific Scimed, (14 pages).
Non final Office Action dated Jul. 13, 2006 for U.S. Appl. No. 10/727,096 filed Dec. 2, 2003, Applicant Boston Scientific Scimed, (10 pages).
Amendment dated May 4, 2006 for U.S. Appl. No. 10/727,096 filed Dec. 2, 2003, Applicant Boston Scientific Scimed, (12 pages).
Final Office Action dated May 7, 2007 for U.S. Appl. No. 10/727,096 filed Dec. 2, 2003, Applicant Boston Scientific Scimed, (8 pages).
Amendment dated Dec. 9, 2005 for U.S. Appl. No. 10/727,096 filed Dec. 2, 2003, Applicant Boston Scientific Scimed, (10 pages).
Non final Office Action dated Aug. 8, 2005 for U.S. Appl. No. 10/727,096 filed Dec. 2, 2003, Applicant Boston Scientific Scimed, (6 pages).

* cited by examiner

FINGER MOUNTABLE LESION FORMATION DEVICES AND METHODS

BACKGROUND OF THE INVENTIONS

1. Field of Inventions

The present inventions relate generally to devices for performing therapeutic operations on body tissue.

2. Description of the Related Art

There are many instances where therapeutic elements must be positioned adjacent to body tissue. One instance involves the formation of therapeutic lesions to the treat cardiac conditions such as atrial fibrillation, atrial flutter and arrhythmia. Therapeutic lesions may also be used to treat conditions in other regions of the body including, but not limited to, the prostate, liver, brain, gall bladder, uterus and other solid organs. Typically, the lesions are formed by ablating tissue with one or more electrodes. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue. The tissue coagulation energy is typically supplied and controlled by an electrosurgical unit ("ESU") during the therapeutic procedure. The amount of power required to coagulate tissue ranges from 5 to 150 W.

A variety of different electrophysiology and electrosurgical devices have been developed for positioning one or more therapeutic elements at the target location. Such devices include catheters, surgical probes and clamps. Although catheters, surgical probes and clamps have proven to be of considerable utility in a wide range of therapeutic procedures, the present inventor has determined that these devices are not well suited for all situations.

In the context of the treatment of atrial fibrillation, for example, conventional electrophysiology and electrosurgical devices have been used to form a set of three transmural encircling lesions that cures paroxysmal atrial fibrillation in most patients. An "encircling lesion," as used herein, is a lesion that extends around a body structure and is not necessarily circular in shape. The lesion set that typically cures paroxysmal atrial fibrillation includes an encircling lesion around the right pulmonary vein pair, an encircling lesion around the left pulmonary vein pair and an encircling lesion around the left atrial appendage. Additional lesions are frequently required for patients with persistent or permanent atrial fibrillation. A transmural "connecting" lesion that connects the lesion around the right pulmonary vein pair to the lesion around the left pulmonary vein pair may be required if these lesions do not overlap, and a transmural connecting lesion that connects the lesion around the left pulmonary vein pair to the lesion around the left atrial appendage may be required if these lesions do not overlap. Finally, a transmural lesion that extends from the mitral valve annulus to one of the lesions described above, must also be formed.

There are many instances where it is desirable to form lesions epicardially, which involves forming the lesions on the outer surface of the heart, in order to avoid catheter based endocardial procedures and more invasive endocardial surgical procedures. Here, conventional electrosurgical clamps may be used to form the epicardial encircling lesions and conventional electrosurgical probes may be used to form the epicardial connecting lesions. With respect to the lesion that extends from the mitral valve annulus to one of the encircling or connecting lesions, the target left atrial tissue is not accessible from the epicardial surface and the present inventor has determined that conventional electrosurgical apparatus and methods are unable to form this lesion from the outer surface of the heart.

SUMMARY OF THE INVENTIONS

A device in accordance with a present invention includes a lesion formation element and a carrier configured to mount the lesion formation element on the physician's finger. There are a number of advantages associated with such a device. For example, the placement of a lesion formation element on the physician's finger facilitates the formation of lesions using techniques that may be impractical with conventional catheters, surgical probes and clamps.

A method in accordance with a present invention includes forming a lesion on the endocardial surface through an invaginated atrial appendage. There are a number of advantages associated with such a method. For example, this method allows a physician to form a lesion that extends from the mitral valve annulus to, for example, an encircling lesion around the atrial appendage without puncturing or cutting through the left atrium.

A method in accordance with a present invention includes mounting a finger mountable lesion formation device on a finger and forming a lesion with the finger mountable lesion formation device. There are a number of advantages associated with such a method. For example, this method facilitates the formation of lesions using techniques that may be impractical with conventional catheters, surgical probes and clamps.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of illustrated embodiments of the inventions will be made with reference to the accompanying drawings.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Exemplary Finger Mountable Lesion Formation Devices
II. Exemplary Lesion Formation Systems
III. Exemplary Lesion Formation Methods The section titles and overall organization of the present detailed description are for the purpose of convenience only and are not intended to limit the present inventions.

This specification discloses a number of structures, mainly in the context of cardiac treatment, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, breasts, uterus and other solid organs.

I. Exemplary Finger Mountable Lesion Formation Devices

Figure 1:
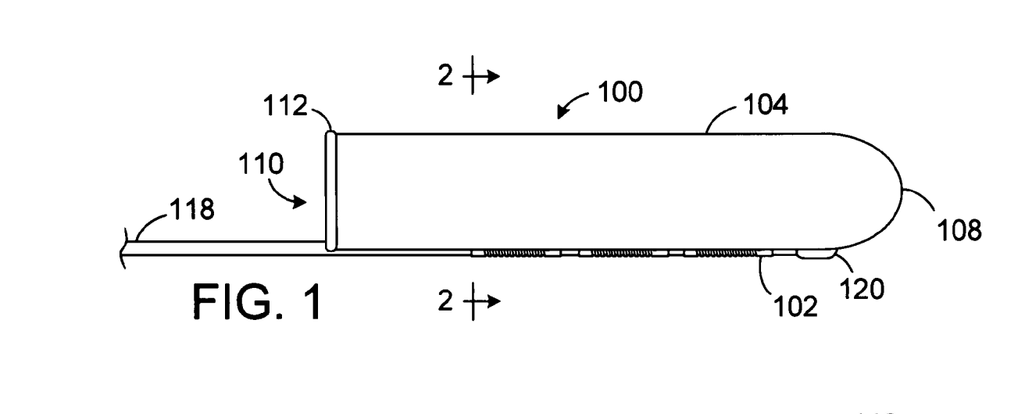
FIG. 1 is side view of a portion of a finger mountable lesion formation device in accordance with one embodiment of a present invention.
Figure 2:
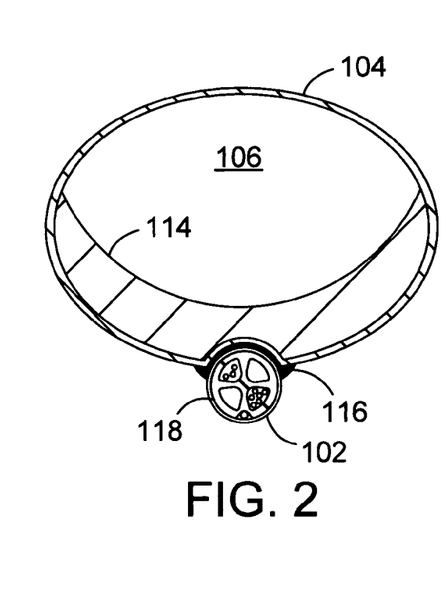
FIG. 2 is a section view taken along line 2-2 in FIG. 1.
Figure 3:
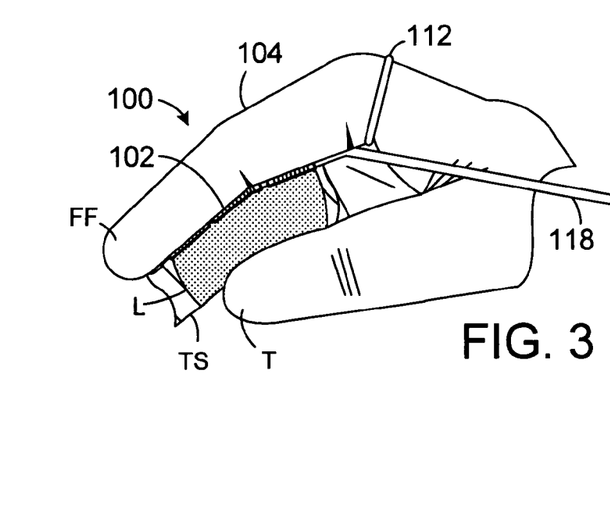
FIG. 3 is a perspective, partial section view showing a lesion being formed with a finger mountable lesion formation device in accordance with one embodiment of a present invention.

As illustrated for example in FIGS. 1-3, a finger mountable lesion formation device 100 in accordance with one embodiment of the present inventions includes one or more electrodes 102 (or other lesion formation elements) and a carrier 104 that performs the function of mounting the electrodes on one of the user's fingers. Although the present inventions are not limited to any particular carrier configuration, the exemplary carrier 104 is a hollow, resilient structure that defines an internal region 106 for the user's finger, a closed end 108 and an open end 110. The internal region 106 will typically be slightly smaller than the expected size of the finger so that the carrier will stretch as the finger enters the internal region and friction force will hold the carrier 104 in place. A ring 112 may be positioned at the open end 110 to help the physician grip the device 100 as it is pulled onto the finger.

The exemplary lesion formation device 100 also includes a thermal insulation element 114 that protects the physician's finger from the heat (or cold) associated with lesion formation procedures. The thermal insulation element 114 extends at least along the combined length of the electrodes 102 or other lesion formation elements and may extend up to the entire length of the carrier 104. The thermal insulation element 114 should also be at least as wide as the electrodes 102 or other lesion formation elements in order to protect the finger from the extreme temperatures (i.e. temperatures that are high or low enough to coagulate tissue) associated therewith. Preferably, however, the thermal insulation element 114 will be considerably wider than the electrodes 102 in order to also protect the finger from the extreme temperatures associated with the target tissue itself. In the exemplary embodiment, the thermal insulation element 114 is co-extensive with about one-half of the circumference of the finger, although the portion of the finger circumference that is covered may be increased or decreased as applications so require. Additionally, it should be noted that although the thermal insulation element 114 is located within the carrier 104 in the exemplary embodiment, it may alternatively be posited between the carrier and the electrodes 102. The thermal insulation element 114 may also be eliminated in those implementations where the carrier 104 has sufficient thermal insulation properties.

Figure 9:
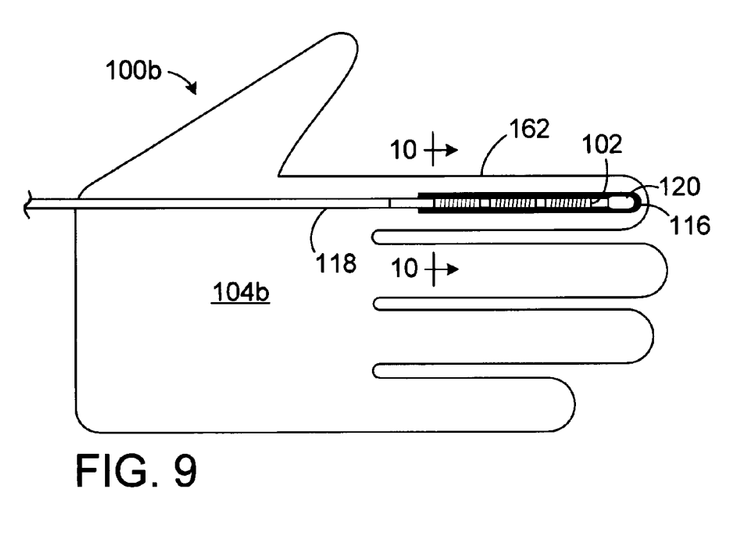
FIG. 9 is plan view of a portion of a finger mountable lesion formation device in accordance with one embodiment of a present invention.

There are a variety of ways to secure the electrodes 102 to the carrier 104. As illustrated for example in FIG. 2, the electrodes 102 may be secured to the carrier 104 through the used of adhesive 116. In the illustrated embodiment, the portion of the thermal insulation element 114 aligned with the electrodes 102 is concaved so that the corresponding portion of the carrier 104 can conform to the curvature of the electrodes over about one-third of the circumference of the electrodes. This may be accomplished by, for example, pressing the electrodes 102 into the carrier 104 and thermal insulation element 114 while the thermal insulation element is in a softened state. The adhesive layer 116 preferably also spreads laterally beyond the electrodes 102 in order to eliminate the sharp corners that would otherwise be defined between the electrodes and the carrier 104, because coagulum could form in these corners. In the exemplary implementation illustrated in FIGS. 1-3, the electrodes 102 are also mounted on an elongate shaft 118 and a tip member 120 is carried on the distal end of the shaft. The shaft 118 and tip member 120 are discussed in greater detail below in the context of FIGS. 4-6. The adhesive layer 116 may, for example, extend from the tip member 120, along the electrodes 102 and along a small portion of the shaft 118 proximal to the proximal-most electrode. This aspect of the exemplary embodiments is illustrated in FIG. 9.

Referring to FIG. 3, the lesion formation device 100 may be mounted on, for example, the physician's forefinger FF and placed against a tissue structure TS. Where practicable, the physician's thumb T may be placed on the opposite side of the tissue structure for support. The electrodes 102 may then be used to form a lesion L in the tissue structure TS. There are a number of benefits associated with the placement of a lesion formation device on the physician's finger. For example, the placement of a lesion formation device on the physician's finger facilitates the formation of lesions using techniques that are impractical with conventional catheters, surgical probes and clamps. Additionally, the device has an atraumatic outer configuration with a large blunt surface area at the distal end that is unlikely to puncture or otherwise damage the left atrial appendage. More specific discussions of exemplary uses of the finger mountable lesion formation device 100 are presented in Section III below.

Figure 4:
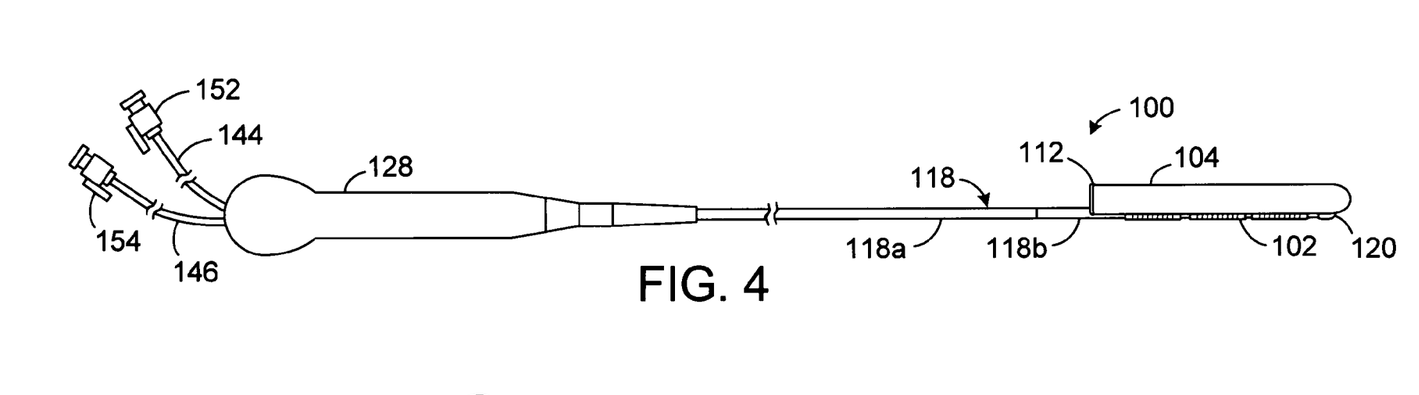
FIG. 4 is side view of a finger mountable lesion formation device in accordance with one embodiment of a present invention.
Figure 5:
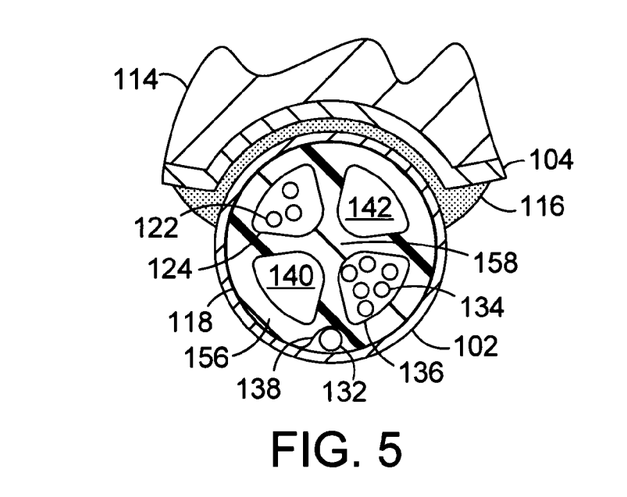
FIG. 5 is an enlarged view of a portion of the section view illustrated in FIG. 2.
Figure 6:
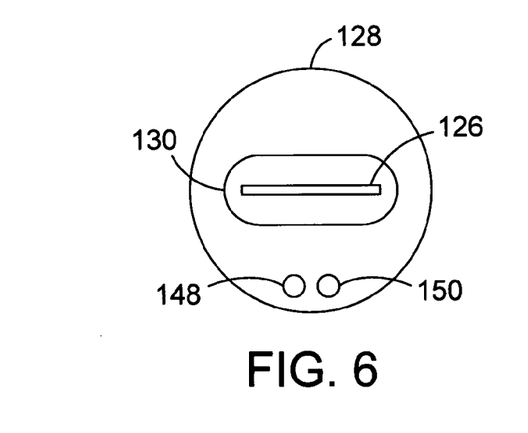
FIG. 6 is an end view of a handle in accordance with one embodiment of a present invention.

Turning to FIGS. 4-6, the electrodes 102 in the exemplary lesion formation device 100 are electrically coupled to power wires 122 that conduct coagulating energy to the electrodes. The power wires 122 are passed, in a manner similar to a conventional catheter, through a lumen 124 in the shaft 118 to a PC board 126 (or other suitable connector) within a handle 128. The handle also includes a slot 130 so that a connector from an ESU may be connected to the PC board 126 in the manner described in Section II below. The handle 128 is not, however, required and is instead provided as a convenient instrumentality to facilitate connection to a conventional ESU. Suitable electrical connectors could, alternatively, simply be provided on the proximal end of the shaft 118.

Preferably, temperature sensors 132 such as thermocouples or thermistors, may be located on, under, abutting the longitudinal end edges of, the electrodes 102. A reference thermocouple (not shown) may also be provided. In the exemplary implementation, temperature sensors 132 are located at the longitudinal ends of the electrodes 102. The temperature sensors 132 are connected to the PC board 126 by signal wires 134 that pass though lumen 136. The temperature sensors 132 are also located within a linear channel 138 that is formed in the shaft distal portion 118b. The linear channel 138 insures that the temperature sensors will face in the same direction (e.g. facing tissue) and be arranged in linear fashion. This arrangement results in more accurate temperature readings which, in turn, results in better temperature control. As such, the actual tissue temperature will more accurately correspond to the temperature set by the physician on the power supply and control device, thereby providing the physician with better control of the lesion creation process and reducing the likelihood that embolic materials will be formed.

The exemplary lesion formation device 100 is a cooled device that employs fluid to cool the electrodes 102. Heat from the electrodes 102 is transferred to the fluid to cool the electrodes while energy is transferred from the electrodes to the tissue. Cooling the electrodes 102 during a coagulation procedure facilitates the formation of lesions that are wider and deeper than those that could be realized with an otherwise identical device which lacks the present cooling capability. Additionally, although gaseous cooling fluid may be employed, liquid is preferred. Referring more specifically to FIGS. 4 and 5, the electrode cooling apparatus in the exemplary finger mountable lesion formation device 100 is composed primarily of the shaft distal portion 118b and fluid inlet and outlet lumens 140 and 142, which are formed in the shaft proximal portion 118a as well as the distal portion. Heat from the electrodes 102 is transferred through the distal portion 118b to fluid that is flowing through the inlet and outlet lumens 140 and 142. Accordingly, in addition to being electrically non-conductive, the material used to form the distal portion 118b should be relatively high in thermal conductivity. As used herein, "relatively high" thermal conductivity is at least about 0.8 W/m·K and preferably ranges from about 0.8 to about 30 (or more) W/m·K.

The inlet lumen 140 is connected to the outlet lumen 142 by a connection lumen (not shown) formed in the tip member 120, which is secured to the shaft distal portion 118b with adhesive or other suitable instrumentalities. The tip member 120 also includes a pair of plugs (not shown) to seal the power and signal wire lumens 124 and 136. The tip member 120 may, alternatively, be replaced by a flexible tube that connects the inlet and outlet lumens 140 and 142. A pair of plugs would be provided for the power and signal wire lumens 124 and 136 when the flexible tube is employed. Fluid may be supplied to the exemplary lesion formation device 100 by way of an infusion lumen 144, which is connected to the inlet lumen 140, and exit by way of a ventilation lumen 146, which is connected to the outlet lumen 142. The infusion and ventilation lumens 144 and 146 extend through a pair of apertures 148 and 150 in the handle 128. The proximal ends of the infusion and ventilation lumens 144 and 146 are provided with on-off valves 152 and 154, which may be connected to a fluid supply device in the manner described in Section II below.

In those instances where the shaft proximal and distal portions 118a and 118b are separate structures, the proximal portion may be larger in diameter than the distal portion because the proximal portion will be for the most part outside the patient. This configuration allows the cross-sectional areas of the fluid inlet and outlet lumens 140 and 142 within the proximal portion 118a to be maximized, thereby minimizing fluid flow resistance. There will be a step-down in the cross-sectional areas of the inlet and outlet lumens 140 and 142 where the proximal portion 118a is secured to the distal portion 118b. In such implementations, the outer diameter of the proximal portion 118a will be about 3 mm to about 5 mm, while the outer diameter of the distal portion 118b will be about 1.66 mm to 3.3 mm.

The exemplary shaft proximal and distal portions 118a and 118b are, as described above, multi-lumen structures and each includes power and signal wire lumens 124 and 136 and fluid inlet and outlet lumens 140 and 142. Alternatively, a single lumen may be provided for the power and signal wires. The power and signal wire lumens may also be eliminated altogether in those instances where the power and signal wires are sufficiently insulated and/or the cooling fluid is sufficiently non-conductive. Another alternative configuration is to arrange the lumens such that the power and signal wire lumens are next to each other. Still another alternative configuration is a central cooling fluid inlet (or outlet) lumen that is connected to an outlet (or inlet) lumen that extends all, or essentially all, of the way around the outer structure. Yet another alternative is provide a tube with a relatively large inner lumen for the shaft proximal portion and series of smaller tubes within the tube to serve as the cooling fluid inlet and outlet lumens and the power and signal wire lumens. The smaller lumens may be connected to the fluid inlet and outlet lumens, as well as the power and signal wire lumens, in the shaft distal portion 118b.

The present inventions also include finger mountable lesion formation devices that are not fluid cooled. Here, the shaft would typically include either pair of lumens for the power and signal wires 122 and 134, or a single lumen for all of the wires.

Although the present inventions are not limited to any particular materials and dimensions, the materials and dimensions of some of the elements in the exemplary finger mountable lesion formation device 100 illustrated in FIGS. 1-6 are discussed below. Turning first to the illustrated lesion formation elements, the exemplary electrodes 102 are flexible coil electrodes made of electrically conducting material, like copper alloy, platinum, or stainless steel, or compositions such as drawn-filled tubing (e.g. a copper core with a platinum jacket). The electrically conducting material can be further coated with platinum-iridium or gold to improve its conduction properties and biocompatibility. Preferred coil electrodes are disclosed in U.S. Pat. Nos. 5,797,905 and 6,245,068.

Alternatively, the electrodes 102 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons or a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form an electrode. Such inks are more flexible than epoxy-based inks. Open coil electrodes may also be employed.

With respect to embodiments intended for use in the heart, for example, the exemplary electrodes 102 are 4 mm to about 20 mm in length. In the illustrated embodiments, the three (3) electrodes 102 are 12.5 mm in length with 1 mm to 3 mm spacing, which will result in an energy transmission region that is about 3-4 cm in length and the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns. Additionally, and regardless of material and size, the present energy transmission devices are not limited to electrodes that extend all the way around the shaft 118. For example, semi-circular electrodes could be mounted on the shaft 118 such that they occupy the spaces occupied by the exposed portion of the electrodes 102 in the illustrated embodiment. The number of electrodes may also be increased and decreased in number as required.

Other types of lesion formation elements, such as infrared lasers, focused and unfocused ultrasonic transducers, microwave electrodes, ohmically heated hot wires, and the like may be substituted for the exemplary electrodes 102. Still another exemplary type of lesion formation element is a cryoablation element. Another exemplary type of lesion formation element is device, such as a jet injector device, that is capable of delivering chemical ablation fluid to tissue. Suitable jet injector devices are disclosed in U.S. Pat. No. 6,814,731, which is incorporated herein by reference.

Turning to the carrier 104, the exemplary carrier is a generally, tubular finger cot-shaped device that is configured to be fit over the index finger, as well as over a surgical glove if worn, and extend slightly beyond the knuckle in the manner illustrated in FIG. 3. As such, the exemplary carrier 104 will typically be about 5 to 8 cm in length. The carrier 104 is also a resilient structure that should be sized such that it will stretch slightly as it is pulled over the finger. Accordingly, the perimeter of the internal region 106 (i.e. the portion of the inside of the carrier not occupied by the insulation element 114, if present) will typically be about 2 to 3 cm, measured about the longitudinal axis of the carrier (note FIG. 2). Suitable materials include elastic, liquid impermeable materials such as latex, polyurethane and thermoplastic elastomers (e.g. Santoprene™) that are about 0.05 to 0.2 mm thick.

The insulation element 114 in the exemplary implementation is about 1 to 6 mm thick at its thickest point, which is suitable for use with most lesion formation elements. Cryoablation elements would, however, typically require a thickness of 2 to 10 mm to adequately protect the finger. The length of the insulation element 114 may range from the length of the electrodes 102, with which it would be aligned, to the length of the carrier 104. Suitable materials include open or closed cell foams, treated leathers such as those used in gloves that are worn in low temperature environments, and insulation fabrics. Other exemplary insulation elements are discussed below with reference to FIGS. 11-13.

With respect to the adhesive 116, suitable adhesives include polymer based adhesives, such as polyurethane based adhesives and elastomer based adhesives (e.g. silicone rubber based adhesives), because these adhesives flexible after curing.

Turning to the exemplary shaft 118, suitable electrically non-conductive, thermally conductive thermoplastics for the shaft distal portion 118b include flexible thermoplastic polymer materials, such as nylon or polyurethane, which are filled with a filler that promotes heat transfer. Suitable fillers include graphite, aluminum, tungsten and ceramic powders. Another suitable filler is Carborundum CarboTherm™ boron nitride powder manufactured by Saint-Gobain in Cavaillon, France. The shaft proximal portion 118a, on the other hand, does not have relatively high thermal conductivity. In those instances where the shaft proximal and distal portions are separate structural elements, the proximal portion 118a may be formed from, for example, flexible non-conductive thermoplastics such as such as Pebax® material and polyurethane. The overall length of the shaft 118 will typically be about 0.5 to 1 m so that the handle 128 can be conveniently placed out of the physician's way during surgical procedures. In those instances where the shaft proximal and distal portions are separate structural elements, the distal portion 118b will occupy about 8 to 15 cm of the overall length.

In addition to the aforementioned fillers, heat transfer may be promoted by minimizing the thickness of the electrically non-conductive material between the inlet and outlet lumens 140 and 142 and the electrodes 102 and by maximizing the cross-sectional area of the inlet and outlet lumens. Referring to FIG. 5, in an implementation where the outer diameter of the shaft distal portion 118b is about 8 French (2.66 mm), the thickness of the outer wall between the electrode 102 and the inlet and outlet lumens 140 and 142 will be about 0.08 mm to about 0.36 mm. It should be noted that when the outer wall thickness is about 0.25 mm or less, materials with less than "relatively high" thermal conductivities, such as Pebax® material and polyurethane, may also be used for the distal portion.

In order to allow the cooling fluid inlet and outlet lumens 140 and 142 to occupy as much of the cross-sectional area and circumferential area of the shaft 118 as possible, the power and signal wire lumens 124 and 136 should be just large enough to accommodate the power and signal wires 122 and 124. The width of the inlet and outlet lumens 140 and 142, i.e. the distance between the outer wall 156 and the inner region 158 (FIG. 5), should be at least 2 times the thickness of outer wall and, preferably 4 times the thickness of the outer wall. In the implementation where the outer diameter of the shaft distal portion 118b is about 8 French (2.66 mm), and the thickness of the outer wall 156 is about 0.1 mm to about 0.25 mm, the width of the inlet and outlet lumens 140 and 142 is preferably about 0.5 mm to about 1.0 mm.

The tip member 120 may be formed from, for example, two molded electrically non-conductive soft plastic parts. Suitable materials include polyurethane and thermoplastic elastomers (e.g. Santoprene™).

Figure 7:
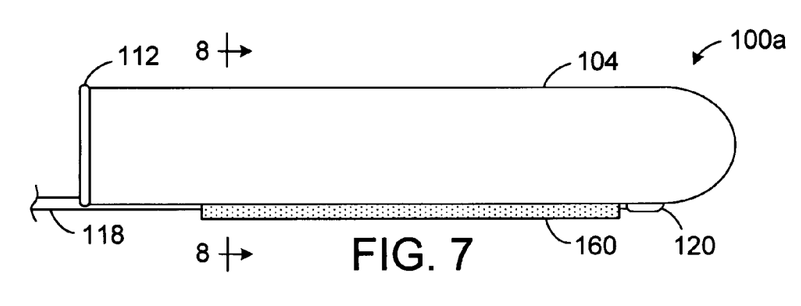
FIG. 7 is side view of a portion of a finger mountable lesion formation device in accordance with one embodiment of a present invention.
Figure 8:
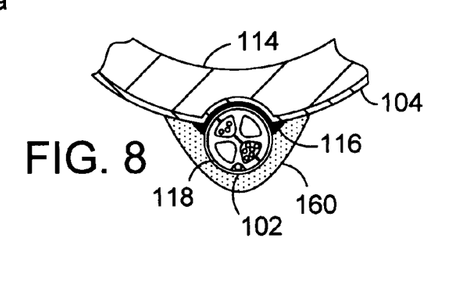
FIG. 8 is a section view taken along line 8-8 in FIG. 7.

Finger mountable lesion formation devices in accordance with the present inventions are not limited to the exemplary implementation illustrated in FIGS. 1-6. As illustrated for example in FIGS. 7 and 8, an exemplary finger mountable lesion formation device 100a, which is otherwise identical to the device described above with reference to FIGS. 1-6, includes a porous, wettable structure 160 that is configured to be saturated with and retain ionic fluid (such as saline) prior to use so that energy may be transmitted from the electrodes 102 by way of the ionic fluid. Suitable materials include foams, such as open cell foams, reticulated foams, non-reticulated foams, fine cell foams and hydrocolloide foams. Other suitable materials include hydrogels, thick woven biocompatible materials (e.g. Dacron®), cotton and cellulose. The thickness of the wettable structure 160 may range from about 0.2 mm to 1 mm and is about 0.5 mm in the illustrated embodiment. Additionally, the electrical resistance of the wettable structure 160 may be reduced by adding conductive fibers thereto (not shown) in the manner described in U.S. application Ser. No. 11/031,630, which is incorporated herein by reference.

Figure 10:
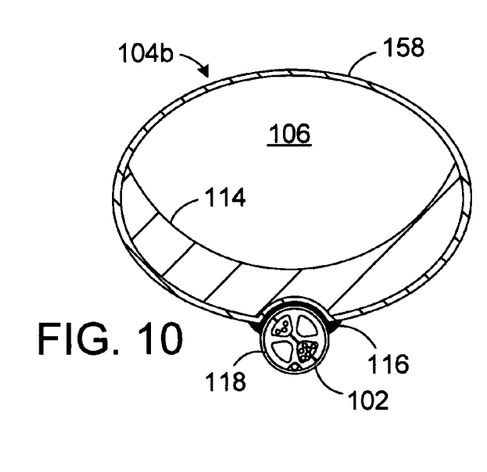
FIG. 10 is a section view taken along line 10-10 in FIG. 9.

Structures other than the finger cot-shaped carrier 104 may also be used to perform the function of mounting the electrodes 102 on one of the user's fingers. Turning to FIGS. 9 and 10, the exemplary finger mountable lesion formation device 100b, which is otherwise identical to the device described above with reference to FIGS. 1-6, includes a carrier in the form of a glove 104b into which the physician may place his or her entire hand. The glove 104b includes a plurality of finger/thumb receiving portions 162 and the electrodes 102 may be secured to any one of the finger/thumb receiving portions. Electrodes may also be positioned on more that one finger, e.g. the thumb and forefinger. Another alternative is to replace finger cot or glove with straps, such as elastic straps, that secure the electrodes 102 to the finger, with the insulation element 114 or other suitable insulation device therebetween. The wettable structure 160 may be positioned over the electrodes 102 in the glove and strap embodiments.

Figure 11:
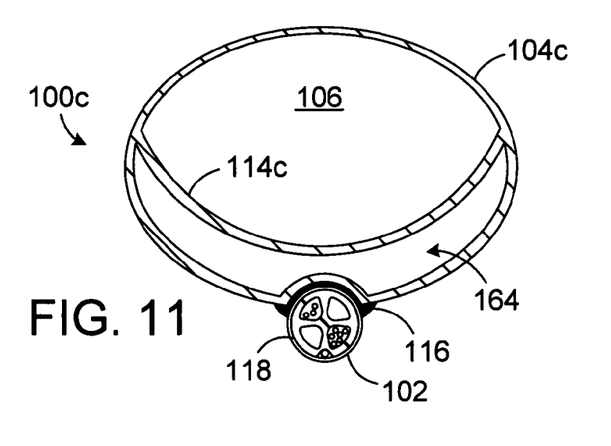
FIG. 11 is a section view of a portion of a finger mountable lesion formation device in accordance with one embodiment of a present invention.

The insulation element 114 is another aspect of the exemplary finger mountable lesion formation devices illustrated in FIGS. 1-10 that is susceptible to variation. Turning to FIG. 11, the exemplary finger mountable lesion formation device 100c, which is otherwise identical to the device described above with reference to FIGS. 1-6, includes an insulation element 114c characterized by a gap 164 that is filled with air or some other gas. A gap thickness of about 0.5 to 4 mm would be suitable for most lesion formation elements, although the gap thickness should be about 1 to 8 mm when cryoablation elements are employed.

Figure 12:
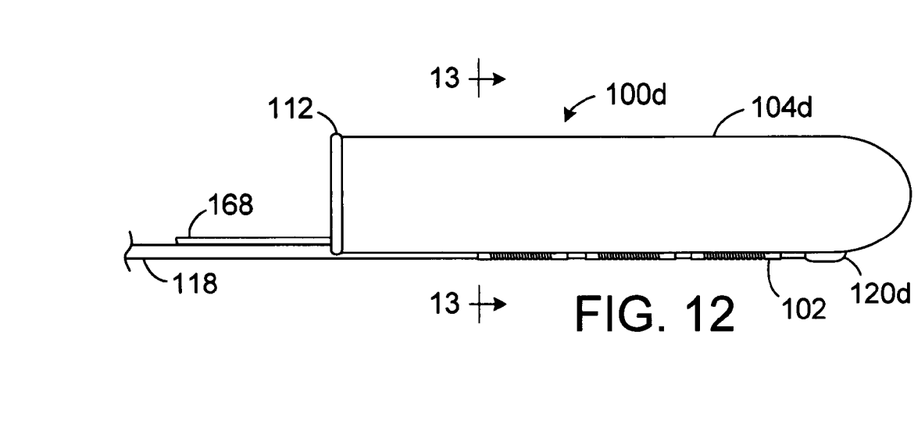
FIG. 12 is side view of a finger mountable lesion formation device in accordance with one embodiment of a present invention.
Figure 13:
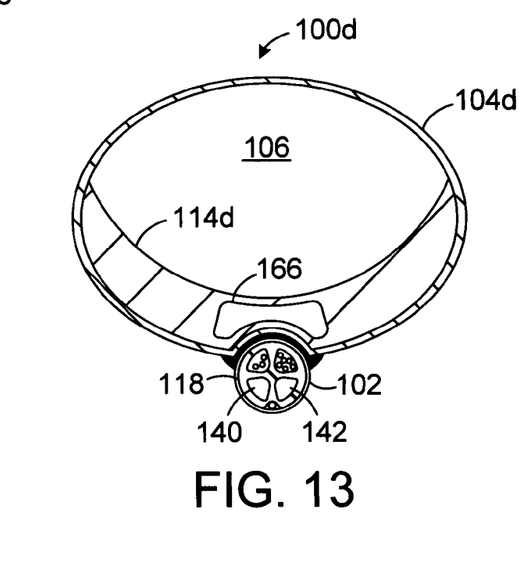
FIG. 13 is a section view taken along line 13-13 in FIG. 12.

The exemplary finger mountable lesion formation device 100d illustrated in FIGS. 12 and 13 is substantially similar to the device described above with reference to FIGS. 1-6. Here, however, both of the fluid lumens 140 and 142 are used as inlet lumens and the insulation element 114d includes a fluid lumen 166. The fluid lumens 140 and 142, which are side-by-side is this embodiment, are connected to the fluid lumen 166 by a connection lumen (not shown) formed in the tip member 120d that meets an aperture (not shown) which extends through the corresponding portions of the carrier 104d and insulation element 114d. An outlet tube 168 is connected to the insulation element fluid lumen 166 and extends proximally into the handle 128 (FIG. 4) where it is connected to the ventilation lumen 146. The fluid lumens 140 and 142 are both connected to the infusion lumen 144 in this embodiment. Accordingly, after the cooling fluid had passed through the shaft lumens 140 and 142, it will pass through the insulation element fluid lumen 166 in order to draw heat away from the physician's finger.

II. Exemplary Systems

Figures 14, 15:
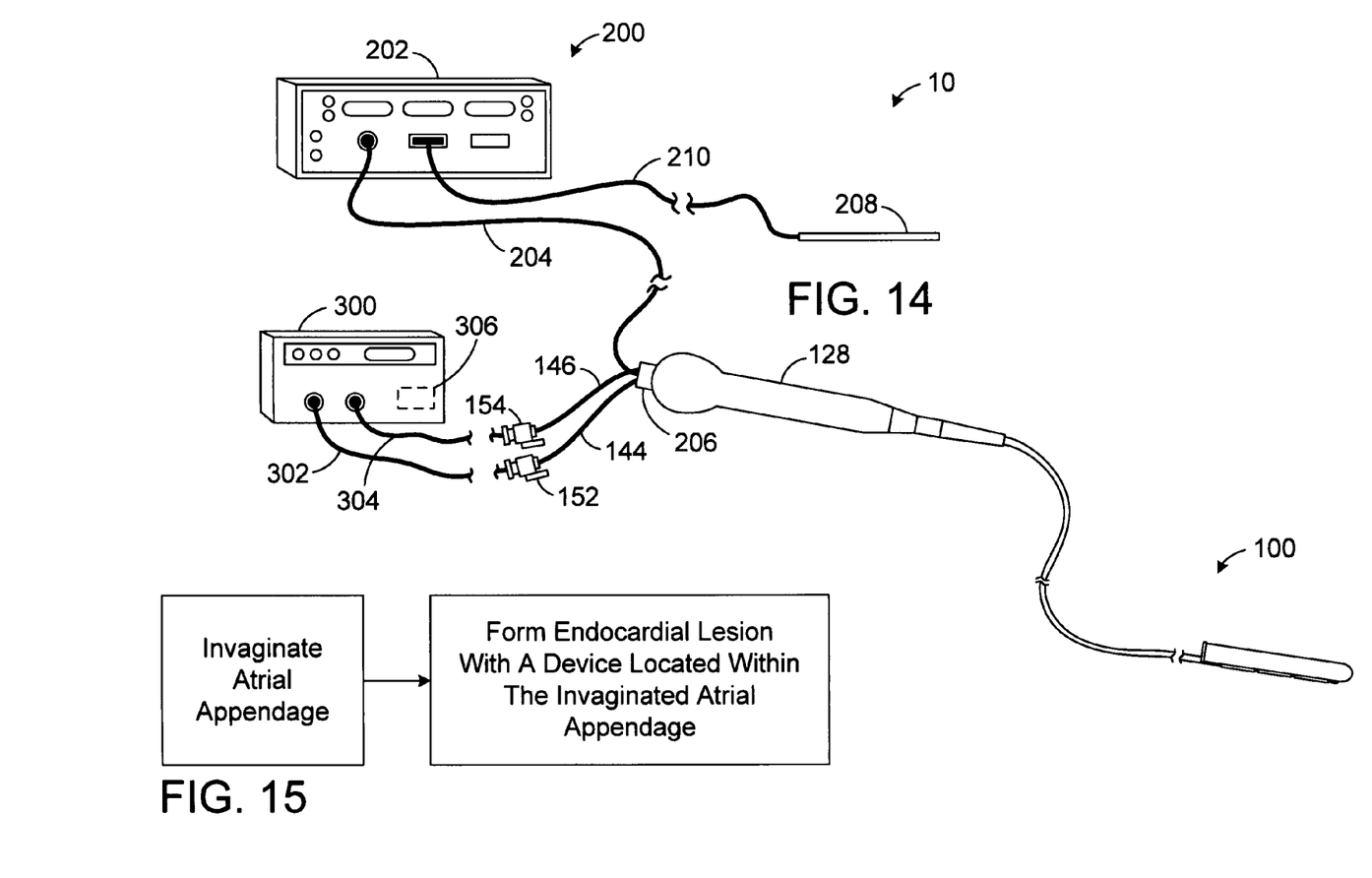
FIG. 14 is a perspective view of a system in accordance with one embodiment of a present invention.
FIG. 15 is a flow chart illustrating a method in accordance with one embodiment of a present invention.

As illustrated for example in FIG. 14, an electrosurgical system 10 in accordance with one embodiment of a present invention includes one of the above-described finger mountable lesion formation devices 100-100d (100 is shown), a power supply and control system 200 and a fluid supply device 300.

The power supply and control system 200 includes an electrosurgical unit ("ESU") 202 that supplies and controls power, such RF power. A suitable ESU is the Model 4810A ESU sold by Boston Scientific Corporation of Natick, Mass. The ESU 202 transmits energy to the electrodes 102 and receives signal from the temperature sensors 132 by way of a cable 204 and a connector 206. The connector 206 is configured to be inserted into the slot 130 (FIG. 6) on the handle 128 and to mate with the PC board 126. The exemplary ESU 202 is operable in a unipolar mode, where the tissue coagulation energy emitted by the electrodes 102 is returned through one or more indifferent electrodes 208 that are externally attached to the skin of the patient with a patch, or one or more electrodes (not shown) that are positioned in the blood pool, and a cable 210. The exemplary ESU 202 may also be operated in bipolar mode where the tissue coagulation energy emitted by one of the electrodes to be returned through one of the other electrodes.

The fluid supply device 300 may be used to supply cooling fluid to the finger mountable lesion formation device 100 (or 100a-100d). To that end, the fluid supply device includes infusion and ventilation lines 302 and 304 that may be respectively connected to the on-off valves 152 and 154 and a control system 306 that may be used to control flow rate. An infusion pump capable of variable flow rates is one example of a suitable fluid supply device. The cooling fluid itself is not limited to any particular fluid. Preferably, however, the fluid will be a low or non-conductive fluid such as sterile water or 0.9% saline solution.

With respect to fluid temperature and flow rate, a suitable inlet temperature is about 0 to 25° C. and the fluid supply device 300 may be provided with a suitable cooling system, if desired, to bring the temperature of the fluid down to the desired level. Although the fluid temperature will rise as heat is transferred to the fluid, the temperature will remain low enough to draw heat from the electrodes 102 as it flows through the inlet and outlet lumens 140 and 142. In a three (3) electrode embodiment such as those illustrated in FIGS. 1-13 where 150 W is being supplied to the electrodes 102, for example, a suitable constant fluid flow rate is about 5 ml/min to about 20 ml/min. In a closed system such as that illustrated in FIG. 14 where the fluid is stored in the fluid supply device 300 and heated fluid is returned to the device, it has been found that a volume of fluid between about 10 and about 60 ml within the device will remain at room temperature (about 22° C.) when the flow rate is between about 5 ml/min. and about 20 ml/min. Alternatively, in an open system where heated fluid is not returned to the fluid supply device 300, the device should include enough fluid to complete the procedure. 60 ml would, for example, be required for a 3 minute procedure where the flow rate was 20 ml/min.

III. Exemplary Methods

Although the present inventions are not limited to any particular therapeutic procedures, one exemplary application of the aforementioned finger mountable lesion formation devices is the formation of lesions associated with the epicardial treatment of persistent or permanent atrial fibrillation. The encircling lesions, i.e. the transmural epicardial lesions around the right pulmonary vein pair, the left pulmonary vein pair and the left atrial appendage, may be formed with an electrosurgical clamp or probe in the manners described in, for example, commonly assigned U.S. Pub. App. No. 2003/0158548 A1 and U.S. Pat. No. 6,786,905, which are incorporated herein by reference. If necessary, the transmural lesions which connect the lesions encircling the right and left pulmonary vein pairs and/or the lesions encircling the left pulmonary vein pair and the left atrial appendage may be formed with an electrosurgical probe. A finger mountable lesion formation device, such as one of the exemplary embodiments described above, may then be used to form a lesion from the mitral valve annulus to any one of the encircling or connecting lesions by way of the left atrial appendage. This may be accomplished with or without a puncture through the left atrial appendage.

With respect to procedures that do not involve a puncture through the left atrial appendage, the physician will invaginate (or turn inside out) the left atrial appendage with the finger on which the finger mountable lesion formation device is mounted. The physician's finger, which is now located within the left atrium, will be covered by the finger mountable lesion formation device which will in turn be covered by the left atrial appendage. Next, the physician will tactilely locate the mitral valve annulus, although a fluoroscope or other suitable device may also be employed. Once the mitral valve annulus has been located, the physician will align his or her finger, as well as the electrodes 102 carried thereon, with tissue on the endocardial surface that extends from the mitral valve annulus to the lesion around the left atrial appendage. Tissue coagulating energy (such as RF energy) may then be supplied to the electrodes 102 to form the transmural lesion from the mitral valve annulus to the lesion around the left atrial appendage. When a lesion is formed by a finger mountable lesion formation device in this manner, the tissue coagulating energy will be applied to the epicardial surface of the left atrial appendage (because it has been invaginated), pass through the left atrial appendage tissue, and then enter the atrial wall tissue from the endocardial side. In other words, an epicardial technique is used to form an endocardial lesion. This method is summarized in FIG. 15.

The method described above may be performed with devices other than finger mountable devices. For example, a therapeutic structure with an atraumatic outer configuration similar to the structure illustrated in FIG. 1 may be carried on the distal end of a surgical probe. The atraumatic therapeutic structure on the surgical probe, which by virtue of the large blunt surface area at the distal end is unlikely to puncture or otherwise damage the left atrial appendage, may be used to invaginate the left atrial appendage and form a lesion in the manner described above.

There are a number advantages associated with the present methods. Most notably, they facilitate the epicardial treatment of persistent or permanent atrial fibrillation by providing an epicardial technique that may be used to form an endocardial lesion that extends from the mitral valve annulus lesion to one of the encircling or connecting lesions.

As noted above, some implementations of the present inventions involve puncturing the left atrial appendage in order to provide an opening into the left atrium for the finger and finger mountable lesion formation device. The puncture replaces the above-described invagination technique. The puncture also allows the electrodes 102 to be placed directly against the endocardial surface, as opposed having atrial appendage tissue between the electrodes and the endocardial surface as is the case when the invagination technique is employed. However, the puncture increases the likelihood of air entering the left atrium, which can cause a stroke, and post-surgery bleeding. Once the appropriate lesion is formed, the puncture will be closed by, for example, a purse string technique.

Although the present inventions have been described in terms of the preferred embodiments above, numerous modifications and/or additions to the above-described preferred embodiments would be readily apparent to one skilled in the art. By way of example, but not limitation, the scope of the inventions includes any combination of the elements from the various species and embodiments disclosed in the specification that are not already described. It is intended that the scope of the present inventions extend to all such modifications and/or additions and that the scope of the present inventions is limited solely by the claims set forth below. Additionally, the present inventions include systems that comprise a power supply device (such as an ESU) and/or a fluid supply device in combination with any of the finger mountable devices claimed below.

I claim:
1. An apparatus, comprising:
a lesion formation element;
a carrier configured to mount the lesion formation element on a human finger; and
an insulation element positioned within the carrier, wherein the lesion formation element is carried on a tubular member that includes a fluid lumen and a wire lumen, and the insulation element includes a fluid lumen operably connected to the fluid lumen in the tubular member.
2. An apparatus as claimed in claim 1, wherein the lesion formation element comprises an electrode.
3. An apparatus as claimed in claim 1, wherein the lesion formation element comprises a plurality of spaced electrodes.
4. An apparatus as claimed in claim 1, wherein the carrier comprises a generally tubular structure.
5. An apparatus as claimed in claim 1, wherein the carrier comprises a glove.
6. An apparatus as claimed in claim 1, wherein the carrier defines an internal region configured to receive the finger, and the insulation element is located between the internal region and the lesion formation element.
7. An apparatus, comprising:
a lesion formation element;
a carrier configured to mount the lesion formation element on a human finger; and
an insulation element positioned between the carrier and the lesion formation element, wherein the lesion formation element is carried on a tubular member that includes a fluid lumen and a wire lumen, and the insulation element includes a fluid lumen operably connected to the fluid lumen in the tubular member.
8. An apparatus as claimed in claim 7, wherein the lesion formation element comprises an electrode.
9. An apparatus as claimed in claim 7, wherein the lesion formation element comprises a plurality of spaced electrodes.
10. An apparatus as claimed in claim 7, wherein the carrier comprises a generally tubular structure.
11. An apparatus as claimed in claim 7, wherein the carrier comprises a glove.
12. An apparatus as claimed in claim 7, wherein the carrier defines an internal region configured to receive the finger, and the insulation element is located between the internal region and the lesion formation element.
13. An apparatus, comprising:
a lesion formation element;
a carrier configured to mount the lesion formation element on a human finger; and
an insulation element associated with the carrier, wherein the lesion formation element is carried on a tubular member that includes a fluid lumen and a wire lumen, and the insulation element includes a fluid lumen operably connected to the fluid lumen in the tubular member.
14. A method, comprising:
forming a lesion on the endocardial surface through an invaginated atrial appendage with a finger mounted device located within the invaginated atrial appendage.
15. A method, comprising:
mounting a finger mountable lesion formation device on a finger;
inserting the finger into a left atrium;
positioning the finger adjacent to tissue within the left atrium; and
forming a lesion in the tissue with the finger mountable lesion formation device.

16. A method as claimed in claim 15, wherein inserting the finger into the left atrium comprises inserting the finger into the left atrium by way of a punctured atrial appendage.

17. A method as claimed in claim 15, wherein inserting the finger into the left atrium comprises inserting the finger into the left atrium by way of an invaginated atrial appendage.

18. A method as claimed in claim 15, wherein forming the lesion comprises forming a lesion from a mitral valve annulus to one of a lesion adjacent to a pulmonary vein and a lesion adjacent to an atrial appendage.

19. A method as claimed in claim 15, wherein forming the lesion comprises forming a lesion by supplying RF energy to the tissue with the finger mountable lesion formation device.

* * * * *